(12) United States Patent
Sekiya et al.

(10) Patent No.: US 6,211,420 B1
(45) Date of Patent: Apr. 3, 2001

(54) PROCESS FOR THE PREPARATION OF FLUORINATED OLEFIN

(75) Inventors: Akira Sekiya, Tsukuba; Toshiro Yamada, Tokyo; Mitsuru Sugawara, Yokohama, all of (JP)

(73) Assignee: Japan as represented by Director General of Agency of Industrial Science and Technology, Tokyo (JP)

( * ) Notice: Subject to any disclaimer, the term of this patent is extended or adjusted under 35 U.S.C. 154(b) by 0 days.

(21) Appl. No.: 09/180,627

(22) PCT Filed: May 2, 1997

(86) PCT No.: PCT/JP97/01516

§ 371 Date: Nov. 13, 1998

§ 102(e) Date: Nov. 13, 1998

(87) PCT Pub. No.: WO97/43233

PCT Pub. Date: Nov. 20, 1997

(30) Foreign Application Priority Data

May 13, 1996 (JP) .................................................. 8-142167

(51) Int. Cl.$^7$ .................................................. C07C 17/20
(52) U.S. Cl. .............................................................. 570/160
(58) Field of Search ............................................... 570/160

(56) References Cited

U.S. PATENT DOCUMENTS 3,567,788 * 3/1971 Carr et al. ............................. 570/160

FOREIGN PATENT DOCUMENTS

| 39-24785 | 11/1964 | (JP) . |
| 62-212331 | 9/1987 | (JP) . |
| 5-508635 | 12/1993 | (JP) . |

* cited by examiner

*Primary Examiner*—Alan Siegel
(74) *Attorney, Agent, or Firm*—Armstrong, Westerman, Hattori, McLeland & Naughton

(57) ABSTRACT

In a process for preparing a fluorinated olefin having a carbon—carbon double bond, the carbon atoms of which have a fluorine atom, by reacting a halogenated olefin having at least one carbon—carbon double bond, a carbon atom or the carbon atoms of which bond have a chlorine atom or atoms bound thereto, and, in which the carbon atom or atoms with a single bond in the molecule have no halogen atom other than a fluorine atom, with an alkali metal fluoride, said reaction of the halogenated olefin with the alkali metal fluoride is conducted in the presence of an organic halogen-containing compound having a carbon—carbon single bond, a carbon or the carbons of which have at least one halogen atom other than fluorine atom.

15 Claims, No Drawings

PROCESS FOR THE PREPARATION OF FLUORINATED OLEFIN

TECHNICAL FIELD

This invention relates to a process for preparing a fluorinated olefin having a carbon—carbon double bond, the carbon atoms of which have a fluorine atom.

BACKGROUND ART

Fluorinated olefins having a carbon—carbon double bond, the carbon atoms of which have a fluorine atom, are used as intermediate materials for fluorinated paraffins used as chlorofluorocarbon alternatives, and monomers for fluorinated polymers, and are produced in a large scale.

Heretofore, these fluorinated olefins have been produced by reacting an olefin compound having a carbon—carbon double bond, the carbon atoms of which have a chlorine atom, with an alkali metal fluoride. For example, 1,2,3,3,4,4,5,5-octafluorocyclopentene is produced by reacting 1,2-dichloro-3,3,4,4,5,5-hexafluorocyclopentene with potassium fluoride [U.S. Pat. No. 3,024,290, ibid. U.S. Pat. No. 3,567,788, and J. Org. Chem., 28, 112(1963)]. However, the yield of the intended product is insufficient for the production thereof in a commercial scale, and thus, enhancement of the yield is desired.

DISCLOSURE OF INVENTION

In view of the foregoing, the object of the invention is to provide an improved process for preparing a fluorinated olefin having a carbon—carbon double bond, the carbon atoms of which have a fluorine atom, by reacting a halogenated olefin having at least one carbon—carbon double bond, a carbon atom or the carbon atoms of which have a chlorine atom, and having the carbon atom or atoms with a single bond having no halogen atom other than a fluorine atom in the molecule, with an alkali metal fluoride, whereby the target fluorinated olefin is produced in an enhanced yield.

Thus, in accordance with the present invention, there is provided a process for preparing a fluorinated olefin having a carbon—carbon double bond, the carbon atoms of which have a fluorine atom, by reacting a halogenated olefin having at least one carbon—carbon double bond, a carbon atom or the carbon atoms of which bond have a chlorine atom or atoms bound thereto, and, in which the carbon atom or atoms with a single bond in the molecule have no halogen atom other than a fluorine atom, with an alkali metal fluoride, characterized in that said reaction of the halogenated olefin with the alkali metal fluoride is conducted in the presence of an organic halogen-containing compound having a carbon—carbon single bond, a carbon or the carbons of which have at least one halogen atom other than fluorine atom.

BEST MODE FOR CARRYING OUT THE INVENTION

Halogenated Olefin

A halogenated olefin used as a stating material in the present invention is that which has at least one carbon—carbon double bond in the molecule, a carbon atom or the carbon atoms of which bond have a chlorine atom or atoms bound thereto, and, in which the carbon atom or atoms with a single bond in the molecule have no halogen atom other than fluorine atom. The halogenated olefin preferably has a fluorine atom or atoms, and the fluorine atom or atoms may be bound to any of the carbon atoms. The number of carbon atoms in the halogenated olefin is not particularly limited, but is usually in the range of from 2 to 30, preferably from 3 to 20 and more preferably from 4 to 10.

As preferable examples of the halogenated olefin, there can be mentioned those which are represented by the following general formula (1):

$$R^1ClC=CClR^2 \qquad (1)$$

wherein $R^1$ and $R^2$ independently represent an alkyl group, a fluoroalkyl group or a fluorine atom, or $R^1$ and $R^2$ may be bonded together to form an alkylene group or a fluoroalkylene group.

When $R^1$ and $R^2$ in the formula (1) are fluoroalkyl groups or bonded together to form a fluoroalkylene group, the reaction takes place rather rapidly and therefore these groups are preferable. The number of carbon atoms in the alkyl, fluoroalkyl, alkylene and fluoroalkylene groups are not particularly limited, but is usually in the range of from 1 to 20, preferably from 2 to 10 and more preferably from 2 to 8.

As specific examples of the alkyl group, there can be mentioned methyl, ethyl, n-propyl, isopropyl, n-butyl, isobutyl, sec-butyl, t-butyl, n-amyl, isoamyl, t-amyl, n-hexyl and n-octyl groups.

As specific examples of the fluoroalkyl group, there can be mentioned fluoromethyl, difluoromethyl, trifluoromethyl, 1,2,2-trifluoroethyl, 1,1,2,2-tetrafluoroethyl, 1,1,1,2,2-pentafluoroethyl, 1,2,2,3,3-pentafluoropropyl, 1,1,2,2,3,3-hexafluoropropyl and 1,1,1,2,2,3,3-heptafluoropropyl groups. Of these, perfluoroalkyl groups such as trifluoromethyl, 1,1,1,2,2-pentafluoroethyl and 1,1,1,2,2,3,3-heptafluoropropyl groups are preferable.

As specific examples of the alkylene group, there can be mentioned propylene, isopropylene, butylene, amylene and hexylene groups are preferable. Of these, propylene, butylene and amylene groups are preferable. A propylene group is most preferable.

As specific examples of the fluoroalkylene group, there can be mentioned 1,1,2,2-tetrafluoropropylene, 1,1,2,2,3-pentafluoropropylene, 1,1,2,2,3,3-hexafluoropropylene, 1,1,2,2,3,3-hexafluorobutylene, 1,1,2,2,3,3,4-heptafluorobutylene and 1,1,2,2,3,3,4,4-octafluorobutylene. Of these, perfluoroalkylene groups such as 1,1,2,2,3,3-hexafluoropropylene and 1,1,2,2,3,3,4,4-octafluorobutylene are preferable. 1,1,2,2,3,3-Hexafluoropropylene is most preferable.

As specific examples of the halogenated olefin, there can be mentioned straight chain halogenated olefin compounds such as 2,3-dichloro-1,1,1,4-tetrafluoro-2-butene, 2,3-dichloro-1,1,1,4,4-pentafluoro-2-butene, 2,3-dichloro-1,1,1,4,4,4-hexafluoro-2-butene, 1,2-dichloro-1,3,3,4-tetrafluoro-1-butene, 1,2-dichloro-1,3,3,4,4-pentafluoro-1-butene, 1,2-dichloro-1,3,3,4,4,4-hexafluoro-1-butene, 1,2-dichloro-1,3,3,4,4,5-hexafluoro-1-pentene, 1,2-dichloro-1,3,3,4,4,5,5-heptafluoro-1-pentene, 1,2-dichloro-1,3,3,4,4,5,5,5-octafluoro-1-pentene, 2,3-dichloro-1,1,1,4,4,5-hexafluoro-2-pentene, 2,3-dichloro-1,1,1,4,4,5,5-heptafluoro-2-pentene and 2,3-dichloro-1,1,1,4,4,5,5,5-octafluoro-2-pentene; and alicyclic halogenated olefin compounds such as 1,2-dichloro-3,3,4,4-tetrafluorocyclopentene, 1,2-dichloro-3,3,4,4,5-pentafluorocyclopentene, 1,2-dichloro-3,3,4,4,5,5-hexafluorocyclopentene, 1,2-dichloro-3,3,4,4,5,5-hexafluorocyclohexene, 1,2-dichloro-3,3,4,4,5,5,6-heptafluorocyclohexene and 1,2-dichloro-3,3,4,4,5,5,6,6-octafluorocyclohexene.

These halogenated olefins may be used either alone or as a combination of at least two thereof.

Organic Halogen-Containing Compound

The organic halogen-containing compound used in the present invention is not particularly limited, provided that it has a carbon—carbon single bond, a carbon or the carbons of which have at least one halogen atom other than fluorine atom. However, in view of the separation and purification of the intended fluorinated olefin, an organic halogen-containing compound capable of reacting with an alkali metal fluoride to give the intended halogenated olefin is preferable. Such organic halogen-containing compound preferably includes those which are represented by the following general formula (2):

$$R^3X^1C=CX^2R^4 \tag{2}$$

wherein $X^1$ and $X^2$ represent a halogen atom, and $R^3$ and $R^4$ independently represent an alkyl group, a haloalkyl group or a halogen atom, or $R^3$ and $R^4$ are bonded together to form an alkylene group or a haloalkylene group, and either $R^3$ or $R^4$ has a halogen atom other than fluorine atom.

$X^1$ and $X^2$ in the formula (2) represent a halogen atom which specifically includes fluorine, chlorine, bromine and iodine atoms. Of these, fluorine and chlorine atoms are preferable. A chlorine atom is most preferable.

$R^3$ and $R^4$ in the formula (2) independently represent an alkyl group, a haloalkyl group or a halogen atom, or $R^3$ and $R^4$ are bonded together to form an alkylene group or a haloalkylene group, and either $R^3$ or $R^4$ has a halogen atom other than fluorine atom. Of these, haloalkyl and haloalkylene groups are preferable. The number of carbon atoms in the alkyl, haloalkyl, alkylene and haloalkylene groups is not particularly limited, but is usually in the range of from 1 to 20, preferably from 2 to 10 and more preferably from 2 to 8.

As specific examples of the alkyl and alkylene groups, there can be mentioned those which are recited as for $R^1$ and $R^2$ in the formula (1).

The halogen in the haloalkyl and haloalkylene groups is characterized as comprising at least one halogen atom other than a fluorine atom. Such halogen atom includes, for example, chlorine, bromine and iodine atoms. These halogen atoms other than a fluorine atom may be used either alone or as a combination of at least two thereof. These halogen atoms may be used in combination with a fluorine atom. Of these, a combination of a chlorine atom with a fluorine atom is preferable.

As specific examples of the haloalkyl group, there can be mentioned chlorofluoromethyl, chlorodifluoromethyl, dichlorofluoromethyl, 1-chloro-2,2-difluoroethyl, 1-chloro-1,2,2-trifluoroethyl, 1,1-dichloro-1,2,2-trifluoroethyl, 1-chloro-1,1,2,2-tetrafluoroethyl, 1-chloro-2,2,3,3-tetrafluoropropyl, 1-chloro-1,2,2,3,3-pentafluoropropyl, 1,1-dichloro-1,2,2,3,3-pentafluoropropyl and 1-chloro-1,1,2,2,3,3-hexafluoropropyl groups. Of these, chlorodifluoromethyl, dichlorofluoromethyl, 1,1-dichloro-1,2,2-trifluoroethyl, 1-chloro-1,1,2,2-tetrafluoroethyl, 1,1-dichloro-1,2,2,3,3-pentafluoropropyl and 1-chloro-1,1,2,2,3,3-hexafluoropropyl groups are preferable. A chlorodifluoromethyl group is especially preferable.

As specific examples of the haloalkylene group, there can be mentioned 1-chloro-1,2,2-trifluoropropylene, 1,3-dichloro-1,2,2-trifluoropropylene, 1-chloro-1,2,2,3-tetrafluoropropylene, 1,3-dichloro-1,2,2,3-tetrafluoropropylene, 1-chloro-1,2,2,3,3-pentafluoropropylene, 2-chloro-1,1,2,3,3-pentafluoropropylene, 2,2-dichloro-1,1,3,3-tetrafluoropropylene, 1,2-dichloro-1,2,3,3- tetrafluoropropylene, 2-chloro-1,1,2,3,3,4,4-heptafluorobutylene, 2,2-dichloro-1,1,3,3,4,4-hexafluorobutylene, 1-chloro-1,2,2,3,3-pentafluorobutylene, 1,4-dichloro-1,2,2,3,3-pentafluorobutylene, 1-chloro-1,2,2,3,3,4-hexafluorobutylene, 1,4-dichloro-1,2,2,3,3,4-hexafluorobutylene and 1-chloro-1,2,2,3,3,4,4-heptafluorobutylenegroups. Of these, 1,3-dichloro-1,2,2,3-tetrafluoroproylene, 2,2-dichloro-1,1,3,3-tetrafluoropropylene, 1-chloro-1,2,2,3,3-pentafluoropropylene, 2-chloro-1,2,2,3,3-pentafluoropropylene, 1,4-dichloro-1,2,2,3,3,4-hexafluorobutylene and 1-chloro-1,2,2,3,3,4,4-heptafluorobutylene groups are preferable. 1,3-Dichloro-1,2,2,3-tetrafluoroproylene, 2,2-dichloro-1,1,3,3-tetrafluoropropylene, 1-chloro-1,2,2,3,3-pentafluoropropylene and 2-chloro-1,2,2,3,3-pentafluoropropylene groups are especially preferable.

These organic halogen-containing compounds may be used either alone or as a combination of at least two thereof. The amount of the halogen-containing compounds can be suitably chosen depending upon the particular reaction conditions and the content of halogen atoms in the molecule, but is usually in the range of from 1 to 200 parts by weight, preferably from 10 to 100 parts by weight and more preferably from 20 to 80 parts by weight, based on 100 parts by weight of the above-mentioned halogenated olefin. If the amount of the organic halogen-containing compound is too small, the yield of the target compound is not enhanced to the desired extent. In contrast, if the amount of the organic halogen-containing compound is too large, the amount of the alkali metal fluoride used is inevitably large which is economically disadvantageous.

Preferable Usage of Halogenated Olefin and Organic Halogen-Containing Compound In the present invention, the above-mentioned halogenated olefin is preferably supplied for the reaction as a mixture thereof with the above-mentioned organic halogen-containing compound. As a preferable example of the mixture, there can be mentioned a reaction product mixture prepared by reacting a perhalogenated conjugated diene and/or a perhalogenated olefin, which have been prepared by substituting the entire hydrogen atoms of conjugated diene by halogen atoms other than a fluorine atom, with hydrogen fluoride.

The perhalogenated conjugated diene, prepared by substituting the entire hydrogen atoms of a conjugated diene by halogen atoms other than a fluorine atom, is not particularly limited, but usually a perchloro-conjugated diene is used. A perchloro-conjugated diene is easily prepared by reacting a conjugated diene hydrocarbon with chlorine gas according to a process, for example, described in British Patent No.1, 070,891. As specific examples of the perchloro-conjugated diene, there can be mentioned aliphatic perchloro-conjugated dienes such as hexachloro-1,3-butadiene, octachloro-1,3-pentadiene, decachloro-1,3-hexadiene and tetradecachloro-1,3-octadiene; and alicyclic perchloro-conjugated dienes such as hexachlorocyclo-1,3-pentadiene, octachlorocyclo-1,3-hexadiene and dodecachlorocyclo-1,3-octadiene. Of these, hexachloro-1,3-butadiene and hexachlorocyclo-1,3-pentadiene are generally used. These perhalogenated conjugated dienes can be used either alone or as a combination of at least two thereof.

The perhalogenated olefin, prepared by substituting the entire hydrogen atoms by halogen atoms other than a fluorine atom, is not particularly limited, but usually perchloroolefins are used because these are readily available.

Perchloroolefins are prepared by reacting the above-mentioned perchloro-conjugated diene further with chlorine gas in the presence of a catalyst such as aluminum trichloride according to a process, for example, described in J. Am. Chem. Soc., 71, 946 (1949). As specific examples of the perchloroolefin, there can be mentioned aliphatic perchloroolefins such as octachloro-1-butene, octachloro-2-butene, decachloro-1-pentene, decachloro-2-pentene, hexadecachloro-1-octene and hexadecachlor-2-octene; and alicyclic perchloroolefins such as octachlorocyclopentene, decachlorocyclohexene and tetradecachlorocyclooctene. Of these, octachloro-2-butene, decachloro-2-pentene, octachlorocyclopentene and decachlorocyclohexene are preferable. Octachlorocyclopentene is especially preferable. These perhalogenated olefins may be used either alone or as a combination of at least two thereof.

The reaction of the perhalogenated conjugated diene or perhalogenated olefin with hydrogen fluoride can be carried out by an ordinary procedure. Usually, hydrogen fluoride is used in an amount of at least 1 equivalent, preferably from 1 to 10 equivalent and more preferably from 1 to 5 equivalent, based on the halogen atoms in the raw material (i.e., perhalogenated conjugated diene or perhalogenated olefin); and the reaction is carried out in the presence of an antimony halide catalyst such as antimony pentachloride, antimony trifluoride dichloride and antimony pentafluoride in an amount of from 0.01 to 20 times by mole, preferably from 0.1 to 10 times by mole and more preferably 0.5 to 5 times by mole, based on the amount of the raw material. The reaction temperature employed is usually in the range of from 20 to 200° C., preferably from 60 to 160° C. and more preferably 80 to 120° C. The reaction pressure employed is usually in the range of from 1 to 30 kg/cm$^2$, preferably from 3 to 20 kg/cm$^2$ and more preferably from 5 to 15 kg/cm$^2$. The reaction time employed is usually in the range of from 0.5 to 48 hours and preferably 1 to 10 hours.

Alkali Metal Fluoride

The alkali metal fluoride used in the present invention is not particularly limited provided that it is used in ordinary chemical reactions. The alkali metal fluoride includes, for example, lithium fluoride, sodium fluoride, potassium fluoride, cesium fluoride and rubidium fluoride. Of these, potassium fluoride, sodium fluoride and cesium fluoride are preferable.

The alkali metal fluoride may be used either alone or as a combination of at least two thereof. The amount of the alkali metal fluoride is usually in the range of from 1 to 3 equivalent weight, preferably from 1.1 to 2.0 equivalent weight and more preferably from 1.2 to 1.5 equivalent weight, based on the total amount of the halogen atoms, other than a fluorine atom, contained in the above-mentioned halogenated olefin and the above-mentioned organic halogen-containing compound. When the amount of the alkali metal fluoride is in this range, the target compound can be produced in a high yield and at a relatively low production cost.

Fluorination Reaction

The fluorination reaction according to the process of the invention is usually carried out in an organic medium. The organic medium used is not particularly limited, but an aprotic polar solvent is preferably used. As specific examples of the polar solvent, there can be mentioned dimethylformamide, dimethylacetamide, N-methylpyrrolidone, N,N-dimethylimidazolidinone, dimethylsulfoxide and sulfolane.

The organic medium may be used either alone or as a mixture of at least two thereof. The amount of the organic medium is, in view of the yield of the target compound, usually in the range of from 100 to 1,000 parts by weight, preferably from 120 to 600 parts by weight and more preferably from 150 to 300 parts by weight, based on 100 parts by weight of the alkali metal fluoride.

The fluorination reaction can be carried out by an ordinary procedure, and usually carried out by heating the above-mentioned primary and secondary raw materials with stirring. The reaction temperature is usually in the range of from 50 to 250° C. and preferably from 80 to 250° C., and the reaction pressure is not particularly limited and may be either a high pressure or a reduced pressure. The reaction time is suitably chosen depending upon the particular reaction conditions and is usually in the range of from 0.5 to 15 hours and preferably from 1 to 9 hours.

The fluorination reaction can be carried out either a batchwise or continuous manner. The fluorinated olefin, i.e., the reaction product has a boiling point lower than those of the halogenated olefin, i.e., substrate, and intermediates produced in the midway of fluorination, and therefore, the reaction is preferably conducted while the reaction product is taken off from a reactor equipped with a fractionating column at the top of the reactor.

In the fluorination reaction according to the invention, the entire amounts of the above-mentioned halogenated olefin and organic halogen-containing compound can be charged in a reactor at once before the initiation of reaction, but preferably at least part of the raw materials is supplied in the midway of reaction. The rate of supply is suitably chosen depending upon the particular rate of the reaction product flowing out from the reactor.

More specifically, it is advantageous from an industrial viewpoint that the fluorination reaction is conducted in an open system by using a reactor equipped with a rectification column, while the above-mentioned halogenated olefin and organic halogen-containing compound are supplied into an organic medium in which an alkali metal fluoride has been dispersed, and the reaction product is taken out. In this process, preferably only the target reaction product is concentrated and isolated with a good purity, and simultaneously, the raw materials and the reaction intermediates are returned back to the reactor as reflux without taking out from the reaction system to the outside.

Utilizing the fact that the fluoroolefin (target product) has a boiling point lower than those of the raw materials and the intermediate products, the raw materials are sequentially supplied to the reaction system comprising a reactor equipped with a rectification column, and simultaneously, the reaction product is taken out from the top of the rectification column. By adopting this procedure, the yield of the fluorinated olefin can be enhanced, and the amount of the reaction medium can be greatly reduced as compared with the conventional procedure. Further, the raw materials and the intermediate products are sequentially returned back to the reactor, and therefore, the amount of the alkali metal fluoride used can be greatly reduced even at a low reaction temperature as compared with the conventional procedure.

The halogenated olefin and the organic halogen-containing compound can be supplied separately, but preferably these raw materials are supplied as a mixture thereof. The rate of supply is chosen depending upon the rate of flow-out of the product. When the supply of the raw materials is excessive, the residence time of the reaction product becomes inevitably long with the result of reduction of yield.

The rate (mol/hr) of supply of the raw materials is usually not larger than three times, preferably from 0.1 to 2 times and more preferably from 0.5 to 1.5 times of the rate (mol/hr) of flow-out of the product.

The reaction product can be obtained by controlling the temperature at the top of the rectification column. The temperature at the top thereof can be set at a temperature approximately equal to the boiling point of the reaction product (which is determined depending upon the pressure) by appropriately setting the reflux ratio so as to conform to the capacity of the rectification column. The recovery of the target product can be carried out by a conventional procedure.

Fluorinated Olefin

The thus-obtained fluorinated olefin is a compound having a carbon—carbon double bond, the carbon atoms of which have a fluorine atom bound thereto. For example, fluorinated olefins represented by the following general formula (3) are obtained from the halogenated olefins represented by the formula (1).

$$R^5FC=CFR^6 \quad (3)$$

wherein $R^5$ and $R^6$ independently represent an alkyl or fluoroalkyl group or a fluorine atom, or $R^5$ and $R^6$ are bonded together to form an alkylene or fluoroalkylene group. As specific examples of $R^5$ and $R^6$ in the formula (3), there can be mentioned those which are hereinbefore recited as for $R^1$ and $R^2$ in the formula (1).

As specific examples of the fluorinated olefin, there can be mentioned 1,1,2,3,3,3-hexafluoropropene, 1,1,2,3,3,4-hexafluoro-1-butene, 1,1,1,2,3,4-hexafluoro-2-butene, 1,1,2,3,3,4,4-heptafluoro-1-butene, 1,1,1,2,3,4,4-heptafluoro-2-butene, 1,1,2,3,3,4,4,4-octafluoro-1-butene, 1,1,1,2,3,4,4,4-octafluoro-2-butene, 1,1,2,3,3,4,4,5-octafluoro-1-pentene, 1,1,1,2,3,4,4,5-octafluoro-2-pentene, 1,1,2,3,3,4,4,5,5-nonafluoro-1-pentene, 1,1,1,2,3,4,4,5,5-nonafluoro-2-pentene, 1,1,2,3,3,4,4,5,5,5-decafluoro-1-pentene, 1,1,1,2,3,4,4,5,5,5-decafluoro-2-pentene, 1,2,3,3,4,4-hexafluorocyclopentene, 1,2,3,3,4,4,5-heptafluorocyclopentene, 1,2,3,3,4,4,5,5-octafluorocyclopentene, 1,2,3,3,4,4,5,5-octafluorocyclohexene, 1,2,3,3,4,4,5,5,6-nonafluorocyclohexene and 1,2,3,3,4,4,5,5,6,6-decafluorocyclohexene.

The invention will now be described in detail by the following working examples that by no means limit the scope of claim of the invention.

PRODUCTION EXAMPLE 1

Preparation of Halogenated Olefin Mixture (I)

A 7-liter stainless steel reactor equipped with a cooling reflux condenser and a pressure-keeping valve was charged with 950 g of antimony pentachloride and 330 g of hexachlorocyclopentadiene, and 100 g of chlorine gas at a pressure of 5 kg/cm² at 80° C. was introduced. The mixture was allowed to react for 2 hours. The unreacted residual chlorine gas was discharged, and 210 g of anhydrous hydrogen fluoride was introduced to allow the hydrogen fluoride to react at a temperature of 84° C. and a pressure of 7 kg/cm² while hydrogen chloride gas produced by a side-reaction was discharged through the pressure-keeping valve. After the generation of hydrogen chloride gas ceased, the pressure was reduced to the normal pressure and the residual hydrogen fluoride was removed, and then, the reaction was further conducted at 140° C. for 5 hours. Simultaneously with the reaction, fractions with a boiling point of from 70 to 100° C. were collected and neutralized with an aqueous sodium bicarbonate solution to give 280 g of a halogenated olefin mixture (I). GC-MS analysis of the mixture (I) revealed that it contained 61.7% by weight of 1,2-dichloro-3,3,4,4,5,5-hexafluorocyclopentene, 30.9% by weight of 1,2,3-trichloro-3,4,4,5,5-pentafluorocyclopentene, 7.1% by weight of 1,2,3,5-tetrachloro-3,4,4,5-tetrafluorocyclopentene and 0.3% by weight of 1,2,3,3,5-pentachloro-4,4,5-trifluorocyclopentene.

PRODUCTION EXAMPLE 2

Preparation of Halogenated Olefin Mixture (II)

The ingredients in the halogenated olefin mixture (I) were separated by fractionation. The thus-separated ingredients were mixed together to prepare a halogenated olefin mixture comprising 80% by weight of 1,2-dichloro-3,3,4,4,5,5-hexafluorocyclopentene, 10% by weight of 1,2,3-trichloro-3,4,4,5, 5-pentafluorocyclopentene and 10% by weight of 1,2,3,5-tetrachloro-3,4,4,5-tetrafluorocyclopentene.

EXAMPLE 1

A 200 ml four-necked flask equipped with a dropping funnel, a rectification column, a thermometer and a stirring device was charged under a nitrogen gas stream with 36.9 g (0.635 mol) of potassium fluoride and 75 ml of dimethylformamide. A cooling medium maintained at −10° C. was circulated into a Dimroth condenser equipped at the top of the rectification column, and a trap for fraction was cooled to −70° C. 51.6 g of the halogenated olefin mixture (I) prepared in Production Example 1 was charged in the dropping funnel, and, when the inner temperature of the flask reached 135° C., the mixture (I) was continuously dropped over a period of 3 hours. When 1.5 hours elapsed from the commencement of reaction, the temperature at the top of the rectification column reached the boiling point of the reaction product (i.e., 27° C.) and was stabilized, and, during the period spanning from this time when the temperature was stabilized to the time when the temperature at the top of column rose, the reaction product was intermittently drawn to give 40.4 g of 1,2,3,3,4,4,5,5-octafluorocyclopentene [purity: 99.9%, yield on the basis of the total halogenated olefin mixture (I): 93.1%].

Comparative Example 1

Fluorination reaction was carried out by the same procedures as employed in Example 1 except that 50.2 g of 1,2-dichloro-3,3,4,4,5,5-hexafluorocyclopentene was used instead of 51.6 g of the halogenated olefin mixture (I) with all other conditions remaining the same. 38.2 g of 1,2,3,3,4,4,5, 5-octafluorocyclopentene was obtained [purity: 99.8%, yield on the basis of 1,2-dichloro-3,3,4,4,5,5-hexafluorocyclopentene: 87.8%].

EXAMPLE 2

Fluorination reaction was carried out by the same procedures as employed in Example 1 except that the halogenated olefin mixture (II) was used instead of the halogenated olefin mixture (I) with all other conditions remaining the same to give 1,2,3,3,4,4,5,5-octafluorocyclopentene [yield on the basis of the total halogenated olefin mixture (II): 92.0%, purity 99.7%].

EXAMPLE 3

Fluorination reaction was carried out by the same procedures as employed in Example 1 except that 96.5 g (0.635 mol, 1.26 equivalent weight on the basis of chlorine atom) of cessium fluoride was used instead of potassium fluoride and 190 ml of dimethylformamide was used. All other conditions remained the same. 40.20 g (0.190 mol) of 1,2,3,3,4,4,5,5-octafluorocyclopentene [yield on the basis of the total halogenated mixture (I): 92.6%, purity: 99.80%] was obtained.

EXAMPLE 4

A halogenated olefin mixture (III) was prepared from octachloro-cyclopentene according to the procedure described in DE-A1 3,935,493. The obtained halogenated olefin mixture (III) contained 80% by weight of 1,2-dichloro-3,3,4,4,5,5-hexafluorocyclopentene and by-products similar to those recited in Example 1.

Fluorination reaction was conducted by the same procedures as employed in Example 1 except that the halogenated olefin mixture (III) was used instead of the halogenated olefin mixture (I) with all other conditions remaining the same to give 1,2,3,3,4,4,5,5-octafluorocyclopentene [yield on the basis of the total halogenated olefin mixture (III): 90.5%].

Industrial Applicability

By the process for preparing a fluorinated olefin according to the present invention, a chlorine atom or atoms bound to a carbon atom or the carbon atoms of the carbon—carbon double bond can be substituted by a fluorine atom, and thus, a corresponding halogenated olefin with a high purity can be produced in a large scale and effectively, and in a high yield with a high purity. Further, in the process of the present invention, a reaction product mixture obtained by reacting a perchloro-conjugated diene or perchloro-olefin with hydrogen fluoride can be used, as it is without purification, as the substrate.

A fluorinated alkane can be produced in a large scale by further hydrogenating the fluorinated olefin prepared by the process of the present invention. The fluorinated olefin and the fluorinated alkane are useful as chlorofluorocarbon alternatives and intermediates therefor, and raw materials for medicines, pesticides, liquid crystals and polymers.

What is claimed is:

1. A process for producing a fluorinated olefin represented by formula (3):

$$R^5FC=CFR^6 \qquad (3)$$

wherein $R^5$ and $R^6$ independently represent an alkyl or fluoroalkyl group or a fluorine atom, or $R^5$ and $R^6$ are bonded together to form an alkylene or fluoroalkylene group, comprising:

reacting a halogenated olefin represented by formula (1):

$$R^1ClC=CClR^2 \qquad (1)$$

wherein $R^1$ and $R^2$ independently represent an alkyl group, a fluoroalkyl group or a fluorine atom, or $R^1$ and $R^2$ are bonded together to form an alkylene group or a fluoroalkylene group, with an alkali metal fluoride, said reaction of the halogenated olefin with the alkali metal fluoride is conducted in the presence of an organic halogen-containing compound represented by formula (2):

$$R^3X^1C=CX^2R^4 \qquad (2)$$

wherein $X^1$ and $X^2$ represent a halogen atom, and $R^3$ and $R^4$ independently represent an alkyl group, a haloalkyl group or a halogen atom, or $R^3$ and $R^4$ are bonded together to form a haloalkylene group, and either $R^3$ or $R^4$ has a halogen atom other than a fluorine atom;

said organic halogen-containing compound of the formula (2) being capable of reacting with the alkali metal fluoride to give the intended halogenated olefin of the formula (3).

2. The process according to claim 1, wherein the amount of the organic halogen-containing compound is in the range of from 1 to 200 parts by weight based on 100 parts by weight of the halogenated olefin.

3. The process according to claim 1, wherein the halogenated olefin has 2 to 30 carbon atoms.

4. The process according to claim 3, wherein the alkyl, fluoroalkyl, alkylene and fluoroalkylkylene groups for $R^1$ and $R^2$ in the formula (1) have from 1 to 20 carbon atoms.

5. The process according to claim 3, wherein $R^1$ and $R^2$ in the formula (1) are a fluoroalkyl group or are bonded together to form a fluoroalkylene group.

6. The process according to claim 1, wherein the halogenated olefin is subjected to the reaction as a mixture thereof with the organic halogen-containing compound.

7. The process according to claim 6, wherein the mixture of the halogenated olefin with the organic halogen-containing compound is a reaction product mixture prepared by reacting at least one compound selected from perhalogenated conjugated dienes and perhalogenated olefins, which have been prepared by substituting the entire hydrogen atoms of conjugated dienes by halogen atoms other than a fluorine atom, with hydrogen fluoride.

8. The process according to claim 1, wherein the amount of the alkali metal fluoride is in the range of from 1 to 3 equivalent based on the amount of the total halogen atoms other than a fluorine atom contained in the sum of the halogenated olefin and the organic halogen-containing compound.

9. The process according to claim 1, wherein the alkali metal fluoride is lithium fluoride, sodium fluoride, potassium fluoride, cesium fluoride or rubidium fluoride.

10. The process according to claim 1, wherein the reaction is carried out in an organic medium.

11. The process according to claim 10, wherein the amount of the organic medium is in the range of from 100 to 1,000 parts by weight based on 100 parts by weight of the alkali metal fluoride.

12. The process according to claim 10, wherein the organic medium is an aprotic polar solvent.

13. The process according to claim 12, wherein the aprotic polar solvent is dimethylformamide, dimethylacetamide, N-methylpyrrolidone, N,N-dimethyl-imidazolidinone, dimethylsulfoxide or sulfolane.

14. The process according to claim 1, wherein the reaction is carried out while the fluorinated olefin is drawn from a reactor which is equipped with a rectification column at the upper part of the reactor.

15. The process according to claim 1, wherein the reaction is carried out in an open system while the halogenated olefin and organic halogen-containing compound are supplied into an organic medium in which the alkali metal fluoride has been dispersed, and while the fluorinated olefin is taken out.

* * * * *

UNITED STATES PATENT AND TRADEMARK OFFICE
CERTIFICATE OF CORRECTION

| | |
|---|---|
| PATENT NO. | : 6,211,420 B1 |
| DATED | : April 3, 2000 |
| INVENTOR(S) | : Akira Sekiya et al. |

It is certified that error appears in the above-identified patent and that said Letters Patent is hereby corrected as shown below:

<u>Title page, item [73],</u>
Add the omitted second Assignee's name:
-- Nippon Zeon Co., Ltd., Tokyo, Japan --.

Signed and Sealed this

Twenty-fifth Day of September, 2001

Attest:

*Nicholas P. Godici*

NICHOLAS P. GODICI
*Attesting Officer*     *Acting Director of the United States Patent and Trademark Office*